United States Patent [19]

Moncada

[11] Patent Number: 4,883,812

[45] Date of Patent: * Nov. 28, 1989

[54] TREATMENT OF HYPERTENSION USING PROSTACYCLIN

[75] Inventor: Salvador Moncada, West Wickham, England

[73] Assignee: Burroughs Wellcome Co., Research Triangle Park, N.C.

[*] Notice: The portion of the term of this patent subsequent to Sep. 3, 2002 has been disclaimed.

[21] Appl. No.: 237,987

[22] Filed: Aug. 29, 1988

Related U.S. Application Data

[63] Continuation of Ser. No. 712,788, Mar. 18, 1985, which is a continuation of Ser. No. 795,524, May 10, 1977, Pat. No. 4,539,333.

[30] Foreign Application Priority Data

Aug. 17, 1976 [GB] United Kingdom ............... 34151

Sep. 3, 1976 [GB] United Kingdom ............... 36547

[51] Int. Cl.$^4$ ............... A61K 31/557; A61K 31/34
[52] U.S. Cl. ............................................. 514/469
[58] Field of Search ............................... 514/469

[56] References Cited

U.S. PATENT DOCUMENTS

| | | | |
|---|---|---|---|
| 4,338,325 | 7/1982 | Johnson et al. | 514/469 |
| 4,430,340 | 7/1984 | Cho | 514/469 |
| 4,499,293 | 2/1985 | Johnson et al. | 549/465 |
| 4,539,333 | 9/1985 | Moncada | 514/469 |

Primary Examiner—Mary C. Lee
Assistant Examiner—Bernard I. Dentz
Attorney, Agent, or Firm—Donald Brown

[57] ABSTRACT

Prostacyclin, its salts biosynthesis and synthesis thereof, pharmaceutical formulations containing them, and their use in medicine.

4 Claims, No Drawings

TREATMENT OF HYPERTENSION USING PROSTACYCLIN

This is a continuation of co-pending application Ser. No. 712,788 filed on Mar. 18, 1985 which is a continuation of Ser. No. 795,524 filed on May 10, 1977 U.S. Pat. No. 4,539,333.

This invention relates to the extraction, isolation and synthesis of a prostaglandin derivative, its use as a chemical intermediate, formulations containing it, and its use in medicine.

Prostaglandin endoperoxides (PGG$_2$ and PGH$_2$) are generated from arachidonic acid by a membrane-bound cyclo-oxygenase enzyme system, described by Hamberg and Samuelsson (Biochem, Biophys. Acta. 326, 448–461,1974) and are subsequently transformed to PGF$_{2\alpha}$, PGE$_2$, PGD$_2$, or Thromboxane A$_2$. Thromboxane A$_2$ shares with the prostaglandin endoperoxides the important biological properties of contracting strips of rabbit aorta and aggregating blood platelets.

The Applicants have now found that microsomes derived from a variety of mammalian tissues catalyse the enzymic transformation of the prostaglandin endoperoxides to a prostaglandin derivative (hereinafter referred to as Prostacyclin which does not contact strips of rabbit aorta, relaxes strips of rabbit coeliac mesenteric and coronary arteries, has a potent anti-aggregatory action on blood platelets, is a strong vasodilator in whole animals and has other properties described hereinafter.

Microsomes derived from rabbit or pig blood vessels such as veins and arteries, and rat stomach fundus produce about 80–90% conversion of the prostaglandin endoperoxides. Microsomes derived from rabbit lung tissue and rat pyloric tissue produce 25% conversion of the prostaglandin endoperoxides, whereas those derived from rat kidney, brain, spleen, liver, heart and seminal vesicle tissues produce 5% or less conversion of the prostaglandin endoperoxides.

Prostacyclin is unstable at room temperature in aqueous medium, having a half-life of approximately 10 mins., but its anti-aggregatory activity can be preserved for several days by dissolving the substance in aqueous alkali or in dry acetone and storing at −20° C. On average prostacyclin is 10–40 times more potent as an anti-aggregatory agent than PGE$_1$ and 5–20 times more potent than PGD$_2$, itself a potent inhibitor of platelet aggregation. Prostacyclin also interrupts and reverses the presence of platelet aggregation.

Prostacyclin may be prepared biosynthetically by incubating PGG$_2$ or PGH$_2$ with aortic microsomes in a suitable buffer solution such as Tris buffer, for approximately 2 minutes at a temperature in the region of 22° C. Conversion of the prostaglandin endoperoxides is approximately 85%.

Extraction of Prostacyclin is achieved by the addition of cold (0° C.) dry diethyl ether to the incubation mixture. The addition of cold ether stops the enzyme reaction and Prostacyclin enters the ether phase which may be separated from the aqueous phase. Evaporation of the ether by standard techniques such as bubbling nitrogen through the solution results in the Prostacyclin being left as a residue which may subsequently be resuspended in an aqueous solution for further examination or dissolved in anhydrous acetone and stored at a temperature in the region of −20° C. for future use.

The aortic microsomes employed in the incubation mixture may be extracted from pig or rabbit aortas. Aortas may be frozen solid preferably by dropping them in liquid nitrogen, and then crushed to form a powder which is resuspended in a suitable buffer solution and subsequently homogenized. The homogenate may then undergo sequential centrifugation so as to isolate the microsomal fraction which may be resuspended in deionized water and lyophilized. The incubation mixture was shown to have an immediate anti-aggregatory effect by monitoring the aggregation of human blood platelets in a Born aggregometer.

Prostacyclin may be prepared using other tissues identified above in substantially a similar manner. Prostacyclin formed in such an incubation mixture appears to be different from the other products of PG endoperoxides so far described. Its biological properties on the isolated tissues, its instability and its potent anti-aggregatory activity show that Prostacyclin is not being PGE$_2$ or PGF$_{2\alpha}$. The presence of prostaglandin D$_2$ isomerase in homogenates of several tissues has been described. As prostacyclin is unstable and is a more potent anti-aggregatory agent than PGD$_2$, it cannot be regarded as PGD$_2$. Furthermore, PGD$_2$ isomerase is present in the 100,000 g. supernatant, a fraction that did not produce Prostacyclin from PG endoperoxides. Moreover, PGD$_2$ isomerase needs glutathione as a cofactor and the incubations were carried out in the absence of cofactors. PGE$_2$, PGF$_{2\alpha}$ and PGD$_2$ were not substrates for aortic microsomes and therefore 15-keto PGs and other products of prostaglandin catabolism could not be considered as Prostacyclin. Prostacyclin is also unlikely to be a known 15-hydroperoxy PG, firstly because 15-hydroperoxy PGE$_2$ has a contractile activity on rabbit aortic strip and secondly the product(s) of the spontaneous decay of Prostacyclin when bioassayed did not behave like PGE$_2$, PGF$_{2\alpha}$, or PGD$_2$. As Prostacyclin has an anti-aggregatory activity it cannot be identical to Thromboxane A$_2$ or B$_2$ as they are pro-aggregatory substances.

Further studies have shown that Prostacyclin has the chemical structure shown in formula (I) (R is hydrogen) (see Johnson et al., Prostaglandins, 12/6, 915–928, 1976).

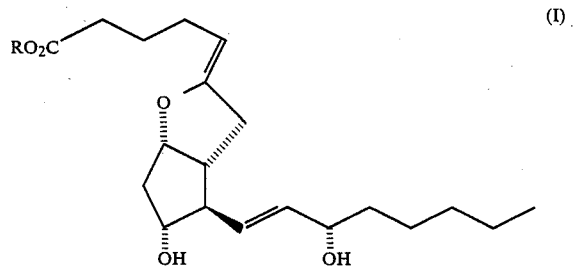

By the present invention we provide the compounds of formula (I) wherein R is hydrogen or a pharmacologically acceptable cation (hereinafter referred to as Prostacyclin and salts thereof). Salts of Prostacyclin include alkali metal salts, alkaline earth metal salts and salts of organic bases.

Salts of Prostacyclin may be synthesised from a compound of formula (II) wherein either or both of Z$^1$ and Z$^2$ is hydrogen or a blocking group such as acyl, or trialkylsilyl (for example trimethylsilyl). Oxidative attack by iodine or potassium triiodide in the presence of a metal bicarbonate at the 5,6-double bond of a compound of formula (II) with simultaneous or subsequent cyclisation involving the 9-hydroxy group produces a compound of formula (III). Upon treatment with a suitable base such as an organic base or a metal alkoxide, a compound of formula (III) may then be dehydrohalogenated, resulting in the introduction of a 5,6-double bond. This reaction sequence is illustrated in the following reaction scheme:

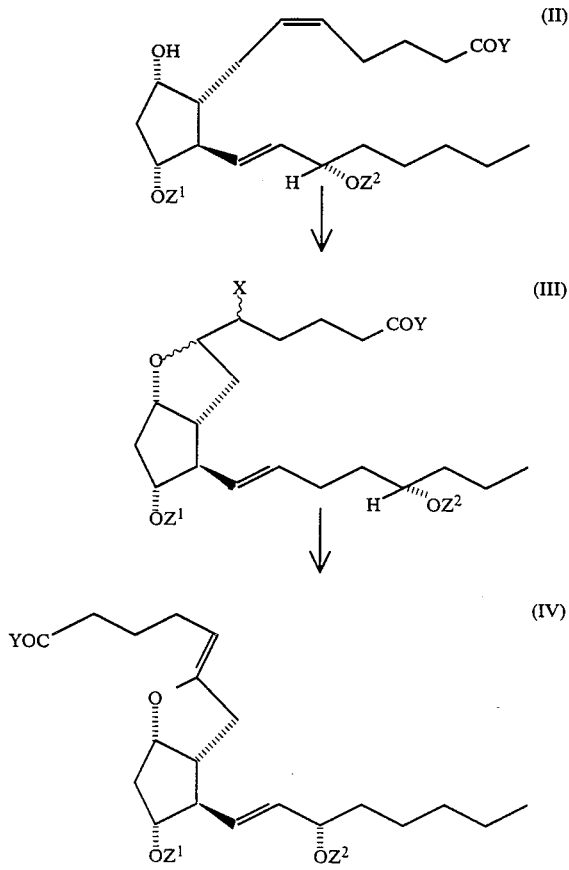

wherein Y is OH, $NHR^1$ or $OR^1$, $R^1$ being alkyl of 1 to 4 carbon atoms or a cation; X is iodo or bromo; and $Z^1$ and $Z^2$ are as defined above.

Included in compounds of formula (IV) are compounds of formula

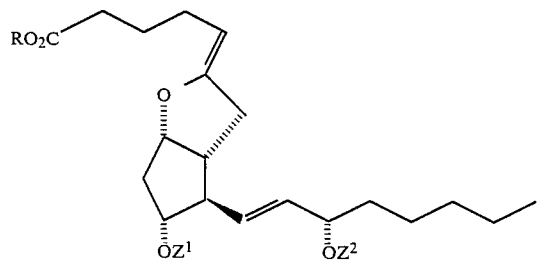

wherein R is hydrogen or a pharmacologically acceptable cation and each of $Z^1$ and $Z^2$ is hydrogen or a blocking group.

When $Z^1$ and/or $Z^2$ in formulae (II), (III) and (IV) are blocking groups, the resulting blocked derivatives of the compounds of formula (I) may be converted to the corresponding compounds of formula (I) by methods known in the art, for example base hydrolysis.

Prostacyclin salts may be prepared by treating an ester thereof (formula (I) : R is alkyl) for example the methyl ester, with a strong base such as sodium hydroxide in a suitable solvent and lyophilising the resulting reaction mixture. Prostacyclin itself may be conveniently prepared by base hydrolysis of its corresponding esters or amides in the presence of an equivalent amount of a caustic alkali in an aqueous alcohol or an aqueous tetrahydrofuran medium, and extracted into an organic solvent at low temperature.

Prostacyclin and its salts are useful as intermediates in the synthesis of prostaglandin analogues, and exhibit a potent anti-aggregatory action on blood platelets, and therefore have a particular utility in the treatment and/or prophylaxis of mammals as anti-thrombotic agents.

They are also useful in mammals, including man, to reduce and control excessive gastric secretion, thereby reducing or avoiding gastrointestinal ulcer formation, and accelerating the healing of such ulcers and lesions already present in the gastrointestinal tract.

Prostacyclin and its salts further exhibit vasodilatory action on blood vessels and therefore have a particular utility as anti-hypertensives for the treatment of high blood pressure in mannals, including man. Use as an antihypertensive may be accomplished by administering a pharmaceutical solution containing the anion of (5Z)-5,6-Didehydro-9-deoxy-6,9-epoxy prostaglandin $F_{1\alpha}$ Platelets can be assimilated into the vascular endothelium or even incorporated into endothelial cells. Biochemical co-operation between platelets and vascular endothelium in the generation of Prostacyclin contributes to the repair of vascular endothelium, and Prostacyclin and its salts have a further utility in the promotion of wound healing in mammals, including man.

Prostacyclin and its salts may be used whenever it is desired to inhibit platelet aggregation, to reduce the adhesive character of platelets, and to treat or prevent the formation of thrombi in mammals, including man. For example, they may be used in the treatment and prevention of myocardial infarcts, λ in the treatment of peripheral vascular disease λ to treat and prevent postoperative thrombosis, to promote patency of vascular grafts following surgery, and to treat complications of arteriosclerosis and conditions such as atherosclerosis, blood clotting defects due to lipemia, and other clinical conditions in which the underlying etiology is associated with lipid imbalance or hyperlipidemia.

They may also be used as additives to blood, blood products, blood substitutes, and other fluids which are used in artificial extra-corporeal circulation and perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of Prostacyclin. For this purpose, Prostacyclin or its salts may be added gradually or in single or multiple portions to the circulating blood, to the blood of the donor animal, to the perfused body portion, attached or detached to the recipient, or to two or all of those at a total steady state dose of 0.001 to 10 mg., per liter of circulating fluid. It is especially useful to use Prostacyclin in laboratory animals, e.g. cats, dogs, rabbits, monkeys and rats, for these purposes in order to develop new methods and techniques for organ and limb transplants.

The amount of prostacyclin or a salt thereof required (hereinafter referred to as the active ingredient) for therapeutic effect will vary with the route of administration. In general a suitable dose for a mammal will lie in the range of 0.01 to 200 mg. per kilogram bodyweight, conveniently 0.01 to 10 mg per kilogram.

While it is possible for the active ingredient to be administered as the raw chemical it is preferable to present it as a pharmaceutical formulation. Such formulations are preferably non-aqueous and non-hydroxylic in nature, but alkaline aqueous solutions may be used. Unit doses of a formulation contain between 0.5 mg. and 1.5 g of the active ingredient.

Such formulations, both for veterinary and for human medical use, of the present invention comprise the active ingredient, as above defined, together with one or more acceptable carriers therefor and optionally other therapeutic ingredeints. The carrier(s) must be "acceptable" in the sense of being compatible with the other ingredients of the formulation and not deleterious to the recipient thereof.

The formulations include those suitable for parenteral (including subcutaneous, intramuscular and intravenous) administrationn which must of course be sterile.

The formulations may conveniently be presented in unit dosage form and may be prepared by any of the methods well known in the art of pharmacy. All methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product into the desired formulation.

According to the present invention there are therefore provided:
(a) the compounds of formula (I) and derivatives thereof blocked in the 11- and 15- positions;
(b) the preparation of Prostacyclin comprising:
   (i) incubation of microsomes of fresh mammalian tissue with a prostaglandin endoperoxide, and the extraction of prostacyclin from the incubation mixture into an organic solvent; or
   (ii) its synthesis as hereinbefore described;
(c) Prostacyclin when obtained by the process described in paragraph (b);
(d) a pharmaceutical formulation containing prostacyclin;
(e) the preparation of such pharmaceutical formulations;
(f) method for the treatment or prophylaxis of thrombosis in a mammal or mammalian tissues, including man, comprising the administration of a non-toxic, prophylactic anti-thrombotic amount of a compound of formula (I).
(g) method for inducing vasodilation in a mammal, including man, comprising the administration of a non-toxic, vasodilatory amount of a compound of formula (I);
(h) method for the prophylaxis or treatment of gastric lesions in a mammal, including man comprising the administration of a non-toxic, prophylactic or therapeutic amount of a compound of formula (I);
(i) (5Z)-5,6-didehydro-9-deoxy-6,9α-epoxy prostaglandin-$F_{1\alpha}$ and its salts (j) method for the promotion of wound healing in a mannal, including man, comprising the administration of a non-toxic wound-treatment amount of a compound of formula (I).

The following examples are provided by way of an illustration of the present invention and should in no way be construed as constituting a limitation thereof.

EXAMPLE 1

Preparation of Prostacyclin

Pig aortas were stripped of adventitia, snap frozen in liquid nitrogen, crushed into a fine powder, resuspended in 0.05 M Tris buffer (pH 7.5) (1:4, w:v) and homogenised at high-speed in a Polytron (KIMENATIC, LUCERNE, SWITZERLAND) homogenizer. The homogenate was centrifuged at 1000 x g for 15 minutes and the resulting supernatant centrifuged again at 10,000 x g for 5 minutes. The 10,000 x g pellet was discarded, while the pellet obtained after centrifugation of the supernatant at 100,000 g for 60 minutes was resuspended in deionized water and lyophilized. An average yield of 150 mg. of aortic microsomal powder (51% protein) per 100 g. of aortic tissue was obtained.

Aortic microsomal powder (5 mg) was incubated with 1 μg of prostalgandin endoperoxide ($PGG_2$ or $PGH_2$) in 0.05M Tris buffer (pH 7.5) (1 ml.) for 2 minutes at 22° C. Enzyme activity was estimated by direct bioassay of the incubation mixture. After incubation of 2 minutes at 22° C. all prostaglandin endoperoxide activity was lost indicated by a lack of contraction of rabbit aorta strips when assayed by the cascade superfusion technique of Vane (Br. J. Pharmac. 23, 369–373, 1964 indicating 100% conversion of $PGG_2$ or $PGH_2$.

The Prostacyclin was extracted by the addition of cold dry diethyl ether (1 ml) to the incubation mixture which also stopped the enzymic reaction. The prostacyclin entered the ether phase, which was subsequently separated from the aqueous phase. The ether was evaporated by bubbling nitrogen through it leaving the Prostacyclin which was either dissolved in ice-cold 0.05M Tris buffer (0.5–1 ml.) and immediately used for platelet aggregation studies or was dissolved in anhydrous acetone (1 ml.) and stored at −20° C. for future use.

The anti-aggregatory activity of the extracted Prostacyclin disappeared on bioling (15 seconds) or on standing at 22° C. for 20 minutes. The anti-aggregatory activity of Prostacyclin could be preserved for several days by dissolving the substance in dry acetone and storing at −20° C.

By using rabbit aortas in a similar experiment the same results were obtained.

EXAMPLE 2

Aggregation of platelets in 1 ml. of fresh human platelet rich plasma (PRP) was monitored in a Born aggregometer. An immediate anti-aggregatory effect of the fresh reaction mixture of Example 1 of aortic microsomes with $PGH_2$ or $PGG_2$ was observed. The lowest anti-aggregatory concentration was obtained with samples containing 0.5–5 ng. Prostacyclin/ml.

This activity disappeared after leaving the incubation mixture for 20 minutes at 22° C. or by bioling for 15 seconds. Aortic microsomes alone (50 μg/ml) could induce aggregation in some PRP. The products of spontaneous degradation of $PGG_2$ (100 ng/ml) had no anti-aggregatory activity.

Diethyl ether extracts of Prostacyclin also inhibited platelet aggregation induced by arachidonic acid and PGG$_2$. The effective anti-aggregatory concentration of Prostacyclin after storate in ether was from 1 to 10 ng/ml.

EXAMPLE 3

Prostacyclin was injected intravenously and intra-aortically into normotensive anaethetised rats and the blood pressure and heart rate recorded. Results shows prostacyclin to be a power vasodepressor having 5 times the potency of PGE$_2$.

EXAMPLE 4

Prostacyclin was found to relax spirally cut strips of coronary artery from the ox. The effect is dose dependent and relaxation can be seen with doses as low as 20 nanograms per 5 ml bath. In isolated hearts from rabbits perfused at constant flow rate by the Langendorf technique, Prostacyclin produced coronary vasodilation.

Prostacyclin relaxed strips of coeliac and mesenteric arteries, but was less potent than PGE$_2$.

EXAMPLE 5

Prostacyclin was shown to inhibit the formation of gastric lesions induced in rats by indomethacin at doses from 62.5 to 250μg upon subcutaneous injection.

EXAMPLE 6

A stirred solution of PGF$_{2\alpha}$ methyl ester (50 mg) in ether (1 ml) was treated with sodium bicarbonate (115.0 mg; 10 molecular equivalents) and water (1 ml) and then dropwise during 2 hours with aqueous potassium triiodide (0.7 molar; 0.261 ml). After stirring overnight, the reaction mixture was shaken with ether and aqueous sodium thiosulphate; the etheral phase was separated, washed with water, dried with magnesium sulphate, and evaporated to leave a yellow gum of 5ξ-iodo-9-deoxy-6ξ,9α-epoxyprostaglandin F$_{1\alpha}$ methyl ester.

A solution of 5ξ-iodo-9-deoxy-6ξ,9α-epoxyprostaglandin F$_{1\alpha}$ methyl ester (100 mg.) in methanolic sodium methoxide prepared from sodium (46 mg.) and dry methanol (0.70 ml.) was set aside under dry nitrogen for 5 hours, then freed from solvent in high vacuum. The residual amorphous solid was washed with benzene, set aside in the air overnight, and stirred with N aqueous sodium hydroxide (0.5 ml.) to give a suspension of colourless fine needles. The crystals were collected, washed with a few drops of N aqueous sodium hydroxide, and dried in the air to give the sodium salt of 9-deoxy-6,9α-epoxy-Δ$^5$-prostaglandin F$_{1\alpha}$. The inhibition of arachidonic acid-induced aggregation of human platelets at a concentration of 0.2 ng./ml. by this salt and its instability in water at acid pH, together with further evidence, is compatible with assignment of the configuration (5Z)-5,6-didehydro-9-deoxy-6,9α-epoxyprostaglandin F$_{1\alpha}$ sodium salt.

The high-resolution $^{13}$C n.m.r. spectrum of a solution of the crystals in dimethyl sulphoxide-d$_6$ showed the expected 20 resonances whose chemical shifts were entirely consistant with the chemical structure established for Prostacyclin. No impurity peaks were detected.

EXAMPLE 7

5ξ-Iodo-9-deoxy-6ξ,9α-epoxyprostaglandin F$_{1\alpha}$ methyl ester (500 mg) was stirred with methanolic NaOMe prepared from Na (0.23 g., 10 equivs.) and MeOH (3.5 ml.) under N$_2$ at room temperature overnight; 1N aq. NaOH (2.5 ml.) was added to the yellow reaction solution to bring about hydrolysis of the ester moiety and, after 2 hours, the methanol was evaporated in vacuo at room temperature. The residual aqueous solution gave rise spontaneously to a mass of colourless fine needles of the desired sodium salt (formula (I): R=Na) which was cooled (0°), collected, washed sparingly with 1N aq. NaOH, air-dried, and stored in a stoppered tube; this salt (383mg.) had λ(KBr disc) νmax 1692 cm$^{-1}$

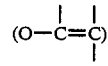

and twenty $^{13}$C resonances only were observed (at 182.7 (C-1), 158.2 (C-6), 140.0 and 134.3 (C-13,14), 100.7(C-5), 87.5(C-15), 80.6 and 75.5(C-9,11), 58.0(C-12), 49.0, 45.8, 42.4, 41.9, 37.5, 35.8 (C-18), 31.6, 29.9, 29.3, 26.7(C-19), and 18.4(C-20) ppm from TMS in DMSO-d$_6$). The product, sodium (5Z)- 5,6-didehydro-9-deoxy-6,9α-epoxyprostaglandin F$_{1\alpha}$ (syn. sodium prostacyclin), thus obtained complete inhibited arachidonic acid-induced platelet aggregation (human platelet-rich plasma) at 1 ng./ml. and its profile of biological activity on the rabbit aorta, rabbit coeliac artery, rat stomach strip and rat colon conformed with that of sodium prostacyclin obtained by biosynthesis. After air-drying, the salt has a surface coating of sodium carbonate (ca 3.5% by weight) which protects the vinyl ether moiety against carbondioxide catalysed hydrolysis.

EXAMPLE 8

5ξ-Iodo-9-deoxy-6ξ,9α-epoxyprostaglandin F$_{1\alpha}$ methyl ester was treated with 1,5-diazabicyclo-5-nonene (DBN) at room temperature in the absence of a solvent for a few hours. The DBN and hydrogen iodide were conveniently removed by adsorption on to a column of SiO$_2$, prepared from a suspension of SiO$_2$ in EtOAc/Et$_3$N 50:1, and the vinyl ether was eluted with the same solvent system. I.R. spectroscopy (thin film, $\nu$ max 1738 (CO$_2$Me) and 1696 cm$^{-1}$

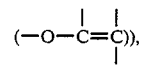

$^1$H n.m.r. in C$_6$D$_6$-Et$_3$N, 19:1 (δ4.22, triplet of triplets$^{12}$, J6.9 and 1.0 Hz (C-5 vinyl proton)), and $^{13}$C n.m.r. in C$_6$D$_6$-Et$_3$N, 19.1 (distinctive features were resonances at 159.8 (C-1), 155.8 (C-6), 137.2 and 130.6 (C-13,14), 95.3 (C-5), 84.1 (C-15) 77.3 and 72.2 (C-9,11) and 51.1. (Me ester)p.p.m. from TMS).

The vinyl ether (5Z)-5,6-didehydro-9-deoxy-6,9α-epoxyprostaglandin methyl ester, was hydrolysed with aqueous sodium hydroxide to give sodium prostacyclin (formula (I): R=sodium).

What we claim is:

1. A method of treating a mammal for hypertension which comprises parenterly administering an effective anti-hypertensive amount of prostacyclin to said mammal.

2. The method of claim 1 in which the prostacyclin is administered by injection as part of a solution.

3. A method of treating a mammal for hypertension which comprises parenterally administering an effective antihypertensive amount of prostacyclin anion in a liquid to said mammal.

4. The method of claim 3 in which the prostacyclin anion is administered by injection.

* * * * *

UNITED STATES PATENT AND TRADEMARK OFFICE

CERTIFICATE EXTENDING PATENT TERM
UNDER 35 U.S.C. § 156

PATENT NO.      :   4,883,812

ISSUED          :   November 28, 1989

INVENTOR(S)     :   Salvador Moncada

PATENT OWNER    :   Glaxo Wellcome Inc.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,347 days from September 3, 2002, the original expiration date of the patent, with all rights pertaining thereto as provided by 35 U.S.C. § 156(b).

I have caused the seal of the Patent and Trademark Office to be affixed this 5th day of September 1997.

Bruce A. Lehman
Assistant Secretary of Commerce and
Commissioner of Patents and Trademarks